(12) United States Patent
Krull et al.

(10) Patent No.: US 8,101,785 B2
(45) Date of Patent: Jan. 24, 2012

(54) METHOD FOR PRODUCING FATTY ACID ALKANOL AMIDES

(75) Inventors: Matthias Krull, Harxheim (DE); Roman Morschhaeuser, Mainz (DE); Peter Klug, Großostheim (DE); Alexander Lerch, Gelnhausen (DE); Christoph Kayser, Mainz (DE); Helmut Ritter, Wuppertal (DE); Sarah Schmitz, Düsseldorf (DE)

(73) Assignee: Clariant Finance (BVI) Limited, Tortola (VG)

( * ) Notice: Subject to any disclaimer, the term of this patent is extended or adjusted under 35 U.S.C. 154(b) by 246 days.

(21) Appl. No.: 12/444,669

(22) PCT Filed: Oct. 5, 2007

(86) PCT No.: PCT/EP2007/008678
§ 371 (c)(1),
(2), (4) Date: Jun. 2, 2009

(87) PCT Pub. No.: WO2008/043493
PCT Pub. Date: Apr. 17, 2008

(65) Prior Publication Data
US 2010/0010244 A1   Jan. 14, 2010

(30) Foreign Application Priority Data
Oct. 9, 2006 (DE) .......... 10 2006 047 615
Nov. 27, 2006 (DE) .......... 10 2006 055 856

(51) Int. Cl.
C07C 231/00 (2006.01)
B01J 19/00 (2006.01)
(52) U.S. Cl. .......... 554/61; 554/49; 554/35; 204/157.82
(58) Field of Classification Search .......... None
See application file for complete search history.

(56) References Cited

U.S. PATENT DOCUMENTS

| | | | |
|---|---|---|---|
| 3,024,260 A * | 3/1962 | Ernst .......... | 554/66 |
| 3,113,026 A | 12/1963 | Sprung | |
| 3,395,162 A * | 7/1968 | Lamberti .......... | 554/66 |
| 3,652,671 A | 3/1972 | Barron | |
| 3,682,946 A | 8/1972 | Liechti | |
| 4,133,833 A | 1/1979 | Hull | |
| 4,582,933 A | 4/1986 | Mertens et al. | |
| 4,675,319 A | 6/1987 | Nardi et al. | |
| 4,859,796 A | 8/1989 | Hurtel et al. | |
| 4,994,541 A | 2/1991 | Dell et al. | |
| 6,017,426 A * | 1/2000 | Semeria et al. .......... | 204/157.88 |
| 2005/0272631 A1 | 12/2005 | Miracle et al. | |
| 2005/0283011 A1 | 12/2005 | Hoong et al. | |
| 2007/0060762 A1 | 3/2007 | Kawashima et al. | |
| 2010/0032284 A1 | 2/2010 | Krull et al. | |
| 2010/0076040 A1 | 3/2010 | Krull et al. | |
| 2010/0081843 A1 | 4/2010 | Krull et al. | |
| 2010/0116642 A1 | 5/2010 | Krull et al. | |

FOREIGN PATENT DOCUMENTS

| | | |
|---|---|---|
| DE | 1139738 | 11/1962 |
| DE | 2009156 | 7/1970 |
| DE | 3209800 | 9/1983 |
| DE | 224203 | 7/1985 |
| EP | 0207901 | 1/1987 |
| EP | 0226501 | 6/1987 |
| EP | 0377177 | 7/1997 |
| EP | 0884305 | 12/1998 |
| EP | 1435364 | 7/2004 |
| WO | WO2004/072031 | 8/2004 |
| WO | WO2005/033062 | 4/2005 |
| WO | WO2005/118526 | 12/2005 |

OTHER PUBLICATIONS

Martinez-Palou, R. et al., Synthesis of long chain 2-allyl-1-(2-hydroxyethyl)-2-imidazolines unde microwave in solvent-free conditions, 2003, Synlett, No. 12, pp. 1847-1849 (3 pages).*
Hunter, R.S., Conversion of visual to instrumental measurements of yellowness, 1981, JAOCS, May, pp. 608-612.*
Synthewave 402 Manual, 2000, Prolabo, Support pages (2) and Manual pp. 1-13 (total 15 pages).*
Kumar, et al., "Microwave Assisted Direct Synthesis of 2-Substituted Benzoxazoles From Carboxylic Acids Under Catalyst and Solvent-Free Conditions", SYNLETT, No. 9, 2005, pp. 1401-1404.
Goretzki et al., Macromol. Rapid Commun. 2004, 25, 513-516.
Gelens et al., Tetrahedron Letters 2005, 46(21), 3751-3754.
M.S. Nery, et al., "Niobium pentachloride promoted conversion of carboxylic acids to carboxamides: Synthesis of the 4-aryl-1,2,3,4-tetrahydroisoquinollne alkaloid structures" Synthesis, (2),272-276, 2003.
Vazquez-Tato, M.P., "Microwave-Mediated Synthesis of Amides", SYNLETT, No. 7, 1993, p. 506.
X. Wu, et al., "Microwave Enhanced Aminocarbonylations in Water", Organic Letters, 7(15), pp. 3327-3329, 2005.
Massicot et al., Synthesis 2001 (16), 2441-2444.
Iannelli et al., Tetrahedron 2005, 61, 1509-1515.
Plantier-Royon, et al., "Synthesis of Functionalized Bis-Amides of L-(+)-Tartaric Acid and Application as Copper(II) Ligands", C.R. Chimie. 2004, pp. 119-123.
Beilstein Substance Identification, BRN No. 6190607, 1981.
Schmitz, et al., "Access to Poly{N-[3-(dimethylamino)propyl](meth)acrylamide} via Microwave-Assisted Synthesis and Control of LCST-Behavior in Water", Macromolecular Rapid Communications, vol. 28, No. 21, Nov. 1, 2007, pp. 2080-2083.
H.J. Bauer, et al., Makromol. Chem., 183, 1982, pp. 2971-2976.
International Search Report for PCT/EP2007/008677 Mail dated Mar. 3, 2008.

(Continued)

*Primary Examiner* — Porfirio Nazario Gonzalez
*Assistant Examiner* — Yate K Cutliff
(74) *Attorney, Agent, or Firm* — Tod A. Waldrop

(57) ABSTRACT

The invention relates to a method for producing fatty acid alkanol amides by reacting at least one amine that contains at least one primary or secondary amino group and at least one hydroxyl group with at least one fatty acid to form an ammonium salt, said ammonium salt being subsequently converted into the alkanol amide by means of microwave radiation.

17 Claims, No Drawings

OTHER PUBLICATIONS

International Search Report for PCT/EP2007/008678 Mail dated Mar. 10, 2008.
International Search Report for PCT/EP2007/008679 Mail dated Feb. 4, 2008.
International Search Report o PCT/EP2007/008680 Mail dated Feb. 15, 2008.
International Search Report for PCT/EP2007/008681 Mail dated Jan. 29, 2008.

* cited by examiner

METHOD FOR PRODUCING FATTY ACID ALKANOL AMIDES

Fatty acid derivatives which bear functional groups with hydrophilic character find widespread use as surface-active substances. An important class of such surface-active substances is that of nonionic amphiphiles which are used to a great extent as emulsifiers, anticorrosives, cooling lubricants in metal processing, as lubricity additives in the mineral oil industry, and also as raw materials for the production of washing compositions, cleaning concentrates, detergents, cosmetics and pharmaceuticals Of particular interest are especially those fatty acid derivatives which bear at least one alkyl radical which is bonded via an amide group and is in turn substituted by at least one hydroxyl group which imparts hydrophilic character. This group can also be derivatized further before the actual use, for example by reaction with alkylene oxides such as ethylene oxide, propylene oxide or butylene oxide, or by oxidation with suitable oxidizing agents. Such amides have greatly increased hydrolysis stability compared to corresponding esters.

In order to cover the growing demand for existing and new applications, various methods have been developed for the preparation of fatty acid amides bearing hydroxyl groups. The preparation of such amides has to date relied on costly and/or laborious preparation processes in order to achieve a yield of commercial interest. The current preparation processes require activated carboxylic acid derivatives, for example acid anhydrides, acid halides such as acid chlorides or esters, which are reacted with amines bearing hydroxyl groups, referred to hereinafter as alkanolamines, or an in situ activation of the reactants by the use of coupling reagents, for example N,N'-dicyclohexylcarbodiimide. Some of these preparation processes form large amounts of undesired by-products such as alcohols, acids and salts, which have to be removed from the product and disposed of. However, the residues of these auxiliary products and by-products which remain in the products can also cause some very undesired effects. For example, halide ions, and also acids, lead to corrosion; some coupling reagents and some of the by-products formed by them are toxic, sensitizing or else carcinogenic.

The direct thermal condensation of carboxylic acid and alkanolamine does not lead to satisfactory results, since various side reactions reduce the yield and in some cases also impair the product properties. One problem is the bisfunctionality of the alkanolamines, which, in addition to the amide formation, also causes a considerable degree of ester formation. Since alkanolamine esters have other properties, for example a significantly lower hydrolysis stability, they are undesired as a by-product in most applications. Furthermore, ester amides, in which both the amino and the hydroxyl group are acylated, in surfactant solutions lead to undesired cloudiness. The ester component can be converted to amides at least partly by thermal treatment, although the color and odor of the alkanolamides thus prepared are very often impaired owing to the long reaction times required for this purpose. However, a removal of the ester components and also of the ester amide components is possible only with difficulty, if at all, owing to the usually very similar physical properties. Further undesired side reactions observed are, for example, a decarboxylation of the carboxylic acid, and oxidation and also elimination reactions of the amino group during the long heating required to achieve high conversions. In general, these side reactions lead to colored by-products, and it is impossible to prepare colorless products which are desired especially for cosmetic applications with Hazen color numbers (to DIN/ISO 6271) of, for example, less than 250. The latter requires additional process steps, for example bleaching, but this in turn requires the addition of further assistants and often leads to a likewise undesired impairment of the odor of the amides or to undesired by-products such as peroxides and degradation products thereof.

A more recent approach to synthesis of amides is the microwave-supported reaction of carboxylic acids with amines to give amides. For instance, Gelens et al., Tetrahedron Letters 2005, 46 (21), 3751-3754, disclose a multitude of amides which have been synthesized with the aid of microwave radiation. One of these is benzoic acid monoethanolamide, which is obtained with a yield of 66%. Massicot et al., Synthesis 2001 (16), 2441-2444 describe the synthesis of diamides of tartaric acid with ethanolamine to achieve a 68% yield of diamide.

EP-A-0 884 305 discloses the amidation of 2-aminooctadecane-1,3-diol with 2-hydroxystearic acid with microwave irradiation to form ceramides with a yield of approx. 70%.

A further increase in conversion in the amidation of benzoic acid or hydroxy-carboxylic acids and alkanolamines does not appear to be possible via the route of microwave irradiation owing to the eliminations which occur as side reactions (decarboxylation of benzoic acid; elimination of water from hydroxycarboxylic acids). These side reactions are particularly disadvantageous both from commercial and ecological aspects, since the by-products formed cannot be recycled into the process but have to be removed and disposed of in a complicated manner.

It was an object of the present invention to find a process for preparing fatty acid alkanolamides, in which fatty acids and amines bearing hydroxyl groups can be converted directly and in high, i.e. up to quantitative, yields to fatty acid alkanolamides. In addition, only minor amounts of by-products, if any, such as, more particularly, paraffins and/or olefins should occur. In addition, fatty acid alkanolamides with a minimum level of intrinsic coloration should form.

It has been found that, surprisingly, fatty acid alkanolamides can be prepared in high yields by microwave irradiation of ammonium salts which derive from amines which bear at least one primary or secondary amino group and at least one hydroxyl group and fatty acids. Surprisingly, virtually no decarboxylation of the fatty acid and no significant ester formation occur. Moreover, the fatty acid amides exhibit virtually no intrinsic coloration.

The invention provides a process for preparing fatty acid alkanolamides by reacting at least one amine which contains at least one primary or secondary amino group and at least one hydroxyl group with at least one fatty acid to give the ammonium salt, and then converting this ammonium salt further under microwave irradiation to the alkanolamide.

The invention further provides fatty acid alkanolamides with a content of esters and ester amides of together less than 5 mol %, preparable by reacting at least one amine which contains at least one primary or secondary amino group and at least one hydroxyl group with at least one fatty acid to give an ammonium salt, and then converting this ammonium salt further under microwave irradiation to the fatty acid alkanolamide.

The invention further provides fatty acid alkanolamides which have a Hazen color number of less than 200, preparable by reacting at least one amine which contains at least one primary or secondary amino group and at least one hydroxyl group with at least one fatty acid to give an ammonium salt, and then converting this ammonium salt further under microwave irradiation to the fatty acid alkanolamide.

The invention further provides fatty acid alkanolamides which are free of halide ions and by-products originating from coupling reagents, preparable by reacting at least one amine which contains at least one primary or secondary amino group and at least one hydroxyl group with at least one fatty acid to give an ammonium salt, and then converting this ammonium salt further under microwave irradiation to the basic amide.

Alkanolamides are understood to mean amides which derive from fatty acids and whose amide nitrogen atom bears at least one hydrocarbon radical substituted by at least one hydroxyl group. Fatty acid amides free of halide ions do not contain any amounts of these ions over and above the ubiquitous amounts of halide ions.

The term "fatty acid" is used here in the sense of monocarboxylic acid. Fatty acids are preferably understood to mean carboxylic acids which bear a hydrocarbon radical having 1 to 50 carbon atoms. Preferred fatty acids have 4 to 50, in particular 6 to 30 and especially 8 to 24 carbon atoms, for example 12 to 18 carbon atoms. They may be of natural or synthetic origin. They may bear substituents, for example halogen atoms, halogenated alkyl radicals, or cyano, hydroxyalkyl, methoxy, nitrile, nitro and/or sulfonic acid groups, with the proviso that they are stable under the reaction conditions and do not enter into any side reactions, for example elimination reactions. The hydrocarbon radicals preferably consist only of carbon and hydrogen. Particularly preferred aliphatic hydrocarbon radicals may be linear, branched or cyclic, and saturated or unsaturated. When they are unsaturated, they may contain one or more, for example two, three or more, double bonds. Preferably, no double bond is in the α,β position to the carboxyl group. The process according to the invention has thus been found to be particularly useful for preparing alkanolamides of polyunsaturated fatty acids, since the double bonds of the unsaturated fatty acids are not attacked. Suitable fatty acids are, for example, octanoic acid, decanoic acid, dodecanoic acid, tridecanoic acid, tetradecanoic acid, 12-methyltridecanoic acid, pentadecanoic acid, 13-methyltetradecanoic acid, 12-methyltetradecanoic acid, hexadecanoic acid, 14-methylpentadecanoic acid, heptadecanoic acid, 15-methylhexadecanoic acid, 14-methylhexadecanoic acid, octadecanoic acid, isooctadecanoic acid, eicosanoic acid, docosanoic acid and tetracosanoic acid, and myristoleic acid, palmitoleic acid, hexadecadienoic acid, delta-9-cis-heptadecenoic acid, oleic acid, petroselic acid, vaccenic acid, linoleic acid, linolenic acid, gadoleic acid, gondoleic acid, eicosadienoic acid, arachidonic acid, cetoleic acid, erucic acid, docosadienoic acid and tetracosenoic acid, and also ricinoleic acid. Additionally suitable are fatty acid mixtures obtained from natural fats and oils, for example cottonseed oil, coconut oil, peanut oil, safflower oil, corn oil, palm kernel oil, rapeseed oil, castor oil, olive oil, mustardseed oil, soybean oil, sunflower oil, and tallow oil, bone oil and fish oil. Likewise suitable as fatty acids or fatty acid mixtures for the process according to the invention are tall oil fatty acid, and resin acids and naphthenic acids.

Alkanolamines suitable in accordance with the invention possess at least one primary or secondary amino group, i.e. at least one amino group bears one or two hydrogen atoms. In addition, at least one alkyl radical bears at least one hydroxyl group. Preferred amines correspond to the formula $HNR^1R^2$ in which $R^1$ ia a hydrocarbon radical which bears at least one hydroxyl group and has 1 to 50 carbon atoms and $R^2$ is hydrogen, $R^1$ or a hydrocarbon radical having 1 to 50 carbon atoms.

$R^1$ bears preferably 2 to 20 carbon atoms, for example 3 to 10 carbon atoms. Additionally preferably, $R^1$ is a linear or branched alkyl radical. This alkyl radical may be interrupted by heteroatoms such as oxygen or nitrogen. $R^1$ may bear one or more, for example two, three or more, hydroxyl groups. The hydroxyl group is, or the hydroxyl groups are each preferably on a primary or secondary carbon atom of the hydrocarbon radical. In the case that $R^2$ is also $R^1$, preference is given to amines which bear a total of at most 5 and especially 1, 2 or 3 hydroxyl groups.

In a preferred embodiment, $R^1$ is a group of the formula $-(B-O)_m-H$ in which B is an alkylene radical having 2 to 10 carbon atoms and
m is from 1 to 500.

B is preferably a linear or branched alkyl radical having 2 to 5 carbon atoms, more preferably a linear or branched alkyl radical having 2 or 3 carbon atoms and especially a group of the formula $-CH_2-CH_2-$ and/or $-CH(CH_3)-CH_2-$.

m is preferably from 2 to 300 and especially from 3 to 100. In a particularly preferred embodiment, m is 1 or 2. Alkoxy chains where m≧3 and especially where m≧5 may be block polymer chains which have alternating blocks of different alkoxy units, preferably ethoxy and propoxy units. They may also be chains with a random sequence of the alkoxy units, or homopolymers.

In a preferred embodiment, $R^2$ is hydrogen, $C_1$-$C_{30}$-alkyl, $C_2$-$C_{30}$-alkenyl, $C_5$-$C_{12}$-cycloalkyl, $C_6$-$C_{12}$-aryl, $C_7$-$C_{30}$-aralkyl or a heteroaromatic group having 5 to 12 ring members. The hydrocarbon radicals may contain heteroatoms, for example oxygen and nitrogen, and optionally substituents, for example halogen atoms, halogenated alkyl radicals, nitro, cyano, nitrile and/or amino groups. $R^2$ preferably represents alkyl radicals having 1 to 18 carbon atoms, especially having 1 to 8 carbon atoms, and alkenyl radicals having 2 to 18 carbon atoms, especially having 2 to 8 carbon atoms. These alkyl and alkenyl radicals may be linear or branched. Suitable alkyl and alkenyl radicals are, for example, methyl, ethyl, propyl, isopropyl, n-butyl, isobutyl, hexyl, decyl, dedecyl, tetradecyl, hexadecyl, octadecyl, isostearyl and oleyl.

In a further preferred embodiment, $R^2$ is an alkyl radical having 1 to 4 carbon atoms, for example methyl or ethyl. In a particularly preferred embodiment, $R^2$ is hydrogen.

The process according to the invention is particularly suitable for preparing fatty acid di(alkanol)amides in which $R^2$ is a group of the formula $-(B-O)_m-H$ in which the definitions of B and m in $R^1$ and $R^2$ may be the same or different. In particular, the definitions of $R^1$ and $R^2$ are the same.

Examples of suitable alkanolamines are aminoethanol, 3-amino-1-propanol, isopropanolamine, N-methyllaminoethanol, N-ethylaminoethanol, N-butylethanolamine, N-methylisopropanolamine, 2-(2-aminoethoxy)ethanol, 2-amino-2-methyl-1-propanol, 3-amino-2,2-dimethyl-1-propanol, 2-amino-2-hydroxymethyl-1,3-propanediol, diethanolamine, dipropanolamine, diisopropanolamine, di(diethylene glycol)amine, N-(2-aminoethyl)ethanolamine, and poly(ether)amines such as poly(ethylene glycol)amine and poly(propylene glycol)amine having in each case 4 to 50 alkylene oxide units.

The process is especially suitable for preparing lauric acid monoethanolamide, lauric acid diethanolamide, lauric acid diglycolamide, coconut fatty acid monoethanolamide, coconut fatty acid diethanolamide, coconut fatty acid diglycolamide, stearic acid monoethanolamide, stearic acid diethanolamide, stearic acid diglycolamide, tall oil fatty acid monoethanolamide, tall oil fatty acid diethanolamide and tall oil fatty acid diglycolamide.

The alkanolamides prepared in accordance with the invention contain, based on the entirety of the fatty acids and fatty acid derivatives present, preferably less than 5 mol %, especially less than 2 mol % and more particularly virtually none of the esters or ester amides resulting from the acylation of the hydroxyl group of the alkanolamine. "Comprising virtually no esters and alkanolamine esters" is understood to mean alkanolamides whose ester and ester amide content is less than 1 mol % and cannot be detected by customary analysis methods, for example $^1$H NMR spectroscopy.

The Hazen color number of the alkanolamides prepared in accordance with the invention is, based on 100% active substance, preferably less than 150 and especially below 100.

The total content of esters and ester amides in the alkanolamides prepared in accordance with the invention is preferably less than 2 mol %, for example less than 1 mol %.

In the process according to the invention, fatty acid and amine can be reacted with one another in any desired ratios. The reaction is preferably effected with molar ratios between fatty acid and amine of 10:1 to 1:10, preferably of 2:1 to 1:2, especially of 1:1.2 to 1.2:1 and more particularly equimolar.

In many cases, it has been found to be advantageous to work with a small excess of amine, i.e. molar ratios of amine to fatty acid of at least 1.01:1.00 and especially between 1.02:1.00 and 1.3:1.0, for example between 1.05:1.0 and 1.1:1. This converts the fatty acid virtually quantitatively to the alkanolamide. This process is particularly advantageous when the alkanolamine used, which bears at least one primary and/or secondary and at least one hydroxyl group, is volatile. "Volatile" here means that the amine has a boiling point at standard pressure of preferably below 200° C., for example below 150° C., and can thus be removed from the amide by distillation.

The inventive preparation of the amides is effected by reacting the fatty acid and the alkanolamine to give the ammonium salt and subsequently irradiating the salt with microwaves. The ammonium salt is preferably obtained in situ and not isolated. Preferably, the temperature rise caused by the microwave irradiation is limited to a maximum of 300° C. by regulating the microwave intensity and/or cooling the reaction vessel. It has been found to be particularly useful to perform the reaction at temperatures between 100 and not more than 250° C. and especially between 120 and not more than 200° C., for example at temperatures between 125 and 180° C.

The duration of the microwave irradiation depends on various factors, such as the reaction volume, the geometry of the reaction chamber and the desired conversion. Typically, the microwave irradiation is undertaken over a period of less than 30 minutes, preferably between 0.01 second and 15 minutes, more preferably between 0.1 second and 10 minutes and especially between one second and 5 minutes, for example between 5 seconds and 2 minutes. The intensity (power) of the microwave radiation is adjusted such that the reaction mixture reaches the desired reaction temperature within a very short time. To subsequently maintain the temperature, the reaction mixture can be irradiated further with reduced and/or pulsed power. To maintain the maximum temperature with simultaneously maximum possible microwave irradiation, it has been found to be useful to cool the reaction mixture, for example by means of cooling jackets, cooling tubes present in the reaction chamber, by intermittent cooling between different irradiation zones and/or by evaporative cooling using external heat exchangers. In a preferred embodiment, the reaction product, directly after the microwave irradiation has ended, is cooled very rapidly to temperatures below 120° C., preferably below 100° C. and especially below 60° C.

The reaction is performed preferably at pressures between 0.1 and 200 bar and especially between 1 bar (atmospheric pressure) and 50 bar. It has been found to be particularly useful to work in closed vessels in which operation is effected above the boiling point of the reactants or products, of any solvent used and/or above the water of reaction formed during the reaction. Typically, the pressure which is established owing to the heating of the reaction mixture is sufficient for successful performance of the process according to the invention. However, it is also possible to work under elevated pressure and/or with application of a pressure profile. In a further preferred variant of the process according to the invention, operation is effected under atmospheric pressure as established, for example, in an open vessel.

To prevent side reactions and to prepare very pure products, it has been found to be useful to perform the process according to the invention in the presence of an inert protective gas, for example nitrogen, argon or helium.

In a preferred embodiment, the reaction is accelerated or completed by working in the presence of dehydrating catalysts. Preference is given to working in the presence of an acidic inorganic, organometallic or organic catalyst, or mixtures of a plurality of these catalysts.

Acidic inorganic catalysts in the context of the present invention include, for example, sulfuric acid, phosphoric acid, phosphonic acid, hypophosphorous acid, aluminum sulfate hydrate, alum, acidic silica and acidic aluminum hydroxide. Also usable as acidic inorganic catalysts are, for example, aluminum compounds of the formula $Al(OR^5)_3$ and titanates of the formula $Ti(OR^5)_4$, where the $R^5$ radicals may each be the same or different and are independently selected from $C_1$-$C_{10}$-alkyl radicals, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, sec-hexyl, n-heptyl, n-octyl, 2-ethylhexyl, n-nonyl or n-decyl, $C_3$-$C_{12}$-cycloalkyl radicals, for example cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl. The $R^5$ radicals in $Al(OR^5)_3$ or $Ti(OR^5)_4$ are preferably each the same and are selected from isopropyl, butyl and 2-ethylhexyl.

Preferred acidic organometallic catalysts are, for example, selected from dialkyltin oxides $(R^5)_2SnO$ where $R^5$ is as defined above. A particularly preferred representative of acidic organometallic catalysts is di-n-butyltin oxide, which is commercially available as so-called oxo-tin or as Fascat® brands.

Preferred acidic organic catalysts are acidic organic compounds with, for example, phosphate groups, sulfonic acid groups, sulfate groups or phosphonic acid groups. Particularly preferred sulfonic acids contain at least one sulfonic acid group and at least one saturated or unsaturated, linear, branched and/or cyclic hydrocarbon radical having from 1 to 40 carbon atoms and preferably having from 3 to 24 carbon atoms. Especially preferred are aromatic sulfonic acids, especially alkylaromatic monosulfonic acids having one or more $C_1$-$C_{28}$-alkyl radicals and especially those having $C_3$-$C_{22}$-alkyl radicals. Suitable examples are methanesulfonic acid, butanesulfonic acid, benzenesulfonic acid, p-toluenesulfonic acid, xylenesulfonic acid, 2-mesitylenesulfonic acid, 4-ethylbenzenesulfonic acid, isopropylbenzenesulfonic acid, 4-butylbenzenesulfonic acid, 4-octylbenzene-sulfonic acid;

dodecylbenzenesulfonic acid, didodecylbenzenesulfonic acid, naphthalenesulfonic acid. It is also possible to use acidic ionic exchangers as acidic organic catalysts, for example sulfo-containing poly(styrene) resins crosslinked with about 2 mol % of divinylbenzene.

For the performance of the process according to the invention, particular preference is given to boric acid, phosphoric acid, polyphosphoric acid and polystyrenesulfonic acids. Especially preferred are titanates of the formula $Ti(OR^5)_4$ and especially titanium tetrabutoxide and titanium tetraisopropoxide.

If the use of acidic inorganic, organometallic or organic catalysts is desired, 0.01 to 10% by weight, preferably 0.02 to 2% by weight, of catalyst is used in accordance with the invention. In a particularly preferred embodiment, no catalyst is employed.

In a further preferred embodiment, the microwave irradiation is performed in the presence of acidic solid catalysts. In this case, the solid catalyst is suspended in the ammonium salt which may have been admixed with solvent or, in continuous processes, the ammonium salt which may have been admixed with solvent is advantageously passed over a fixed catalyst bed and exposed to microwave radiation. Suitable solid catalysts are, for example, zeolites, silica gel, montmorillonite and (partly) crosslinked polystyrenesulfonic acid, which may optionally be impregnated with catalytically active metal salts. Suitable acidic ion exchangers based on polystyrenesulfonic acids, which can be used as solid phase catalysts, are obtainable, for example, from Rohm & Haas under the Amberlyst® brand.

It has been found to be useful to work in the presence of solvents, in order, for example, to lower the viscosity of the reaction medium, to fluidize the reaction mixture, if it is heterogeneous, and/or to improve the removal of heat, for example by means of evaporative cooling. For this purpose, it is possible in principle to use all solvents which are inert under the reaction conditions employed and do not react with the reactants or the products formed. An important factor in the selection of suitable solvents is their polarity, which first determines the dissolution properties and secondly the extent of interaction with microwave radiation. A particularly important factor in the selection of suitable solvents is their dielectric loss $\in''$. The dielectric loss $\in''$ describes the proportion of microwave radiation which is converted to heat on interaction of a substance with microwave radiation. The latter value has been found to be a particularly important criterion for the suitability of a solvent for the performance of the process according to the invention. It has been found to be particularly useful to work in solvents which exhibit a minimum microwave absorption and hence make only a small contribution to the heating of the reaction system. Solvents preferred for the process according to the invention possess a dielectric loss $\in''$, measured at room temperature and 2450 MHz, of less than 10 and preferably less than 1, for example less than 0.5. An overview of the dielectric loss of various solvents can be found, for example, in "Microwave Synthesis" by B. L. Hayes, CEM Publishing 2002. Especially suitable for the process according to the invention are solvents with $\in''$ values below 10, such as N-methylpyrrolidone, N,N-dimethylformamide or acetone, and especially solvents having $\in''$ values below 1. Examples of particularly preferred solvents with $\in''$ values below 1 are aromatic and/or aliphatic hydrocarbons, for example toluene, xylene, ethylbenzene, tetralin, hexane, cyclohexane, decane, pentadecane, decalin and commercial hydrocarbon mixtures such as petroleum fractions, kerosene, solvent naphtha, ®Shellsol AB, ®Solvesso 150, ®Solvesso 200, ®Exxsol, ®Isopar and ®Shellsol types. Solvent mixtures which have $\in''$ values preferably below 10 and especially below 1 are equally preferred for the performance of the process according to the invention. In principle, the process according to the invention is also possible in solvents with $\in''$ values of 10 and higher, but this requires special measures for maintaining the maximum temperature and often leads to reduced yields. When working in the presence of solvents, the proportion thereof in the reaction mixture is preferably between 2 and 95% by weight, especially between 5 and 90% by weight and more particularly between 10 and 75% by weight, for example between 30 and 60% by weight. The reaction is more preferably performed without solvent.

The microwave irradiation is typically performed in units which possess a reaction chamber composed of a material very substantially transparent to microwaves, into which microwave radiation generated in a microwave generator is injected by means of suitable antenna systems. Microwave generators, for example the magnetron and the klystron, are known to those skilled in the art.

Microwaves refer to electromagnetic rays having a wavelength between about 1 cm and 1 m and frequencies between about 300 MHz and 30 GHz. This frequency range is suitable in principle for the process according to the invention. Preference is given to using, for the process according to the invention, microwave radiation with the frequencies approved for industrial, scientific and medical applications of 915 MHz, 2.45 GHz, 5.8 GHz or 27.12 GHz. It is possible to work either in monomode or quasi-monomode, or else in multimode. In the case of monomode, which places high demands on the geometry and size of apparatus and reaction chamber, a very high energy density is generated by a standing wave, especially at the maximum thereof. In multimode, in contrast, the entire reaction chamber is irradiated substantially homogeneously, which enables, for example, greater reaction volumes.

The microwave power to be injected into the reaction vessel for the performance of the process according to the invention is dependent especially on the geometry of the reaction chamber and hence on the reaction volume, and on the duration of the irradiation required. It is typically between 100 W and several hundred kW, and especially between 200 W and 100 kW, for example between 500 W and 70 kW. It can be applied at one or more sites in the reactor. It can be generated by means of one or more microwave generators.

The reaction can be carried out batchwise or preferably continuously in a flow tube, for example. It can additionally be performed in semibatchwise processes, for example continuous stirred reactors or cascade reactors. In a preferred embodiment, the reaction is performed in a closed vessel, in which case the condensate which forms and if appropriate reactants and, where present, solvents lead to a pressure buildup. After the reaction has ended, the elevated pressure can be used by decompression to volatilize and remove water of reaction, and if appropriate solvents and excess reactants, and/or cool the reaction product. In a further embodiment, the water of reaction formed, after cooling and/or decompression, is removed by customary processes, for example phase separation, distillation and/or absorption. The process according to the invention can be effected equally successfully in an open vessel with evaporative cooling and/or separation of the water of reaction.

In a preferred embodiment, the process according to the invention is performed in a batchwise microwave reactor. The microwave irradiation is undertaken in a stirred vessel. To remove excess heat, cooling elements are preferably present in the reaction vessel, for example cooling fingers or cooling coils, or reflux condensers flanged onto the reaction vessel for evaporative cooling of the reaction medium. For the irradiation of relatively large reaction volumes, the microwave here is preferably operated in multimode. The batchwise embodiment of the process according to the invention allows, through variation of the microwave power, rapid or else slow heating rates, and especially the maintenance of the temperature over prolonged periods, for example several hours. The reactants and any solvents and further assistants can be initially be charged in the reaction vessel before commencement of the microwave irradiation. They preferably have temperatures below 100° C., for example between 10° C. and 50° C. In a further embodiment, the reactants or portions thereof are not added to the reaction vessel until during the irradiation with microwaves. In a further preferred embodiment, the batchwise microwave reactor is operated with continuous supply of reactants and simultaneous discharge of reaction mixture in the form of a semibatchwise or cascade reactor.

In a particularly preferred embodiment, the process according to the invention is performed in a continuous microwave reactor. To this end, the reaction mixture is conducted through a pressure-resistant reaction tube which is inert toward the reactants, is very substantially transparent to microwaves and is installed into a microwave oven. This reaction tube preferably has a diameter of from one millimeter to approx. 50 cm, especially between 1 mm and 35 cm, for example between 2 mm and 15 cm. Reaction tubes are understood here to mean vessels whose ratio of length to diameter is greater than 5, preferably between 10 and 100 000, more preferably between 20 and 10 000, for example between 30 and 1000. In a specific embodiment, the reaction tube is configured in the form of a jacketed tube through whose interior and exterior the reaction mixture can be conducted successively in countercurrent, in order, for example, to increase the thermal conduction and energy efficiency of the process. The length of the reaction tube is understood to mean the total distance through which the reaction mixture flows. Over its length, the reaction tube is surrounded by at least one microwave radiator, but preferably more than one, for example two, three, four, five, six, seven, eight or more microwave radiators. The microwaves are preferably injected through the tube jacket. In a further preferred embodiment, the microwaves are injected by means of at least one antenna via the tube ends. The reaction tube is typically provided at the inlet with a metering pump and a manometer, and at the outlet with a pressure-retaining valve and a heat exchanger. The alkanolamine and fatty acid reactants, both independently optionally diluted with solvent, are preferably not mixed until shortly before entry into the reaction tube. Additionally preferably, the reactants are supplied to the process according to the invention in liquid form with temperatures below 100° C., for example between 10 and 50° C. To this end, higher-melting reactants can be used, for example, in the molten state or admixed with solvent.

Variation of tube cross section, length of the irradiation zone (this is understood to mean the proportion of the reaction tube in which the reaction mixture is exposed to microwave irradiation), flow rate, geometry of the microwave radiators, the microwave power injected and the temperature attained as a result are used to adjust the reaction conditions such that the maximum reaction temperature is attained as rapidly as possible and the residence time at maximum temperature remains sufficiently short that as low as possible a level of side reactions or further reactions occurs. Preference is given to operating the continuous microwave reactor in monomode or quasi-monomode. The residence time in the reaction tube is generally less than 30 minutes, preferably between 0.01 second and 15 minutes and preferably between 0.1 second and 5 minutes, for example between one second and 3 minutes. To complete the reaction, if appropriate after intermediate cooling, the reaction mixture can pass through the reactor more than once. It has been found to be particularly useful when the reaction product, immediately after leaving the reaction tube, is cooled, for example by jacket cooling or decompression.

It was particularly surprising that, in spite of the only very short residence time of the ammonium salt in the microwave field in the flow tube with continuous flow, such a substantial amidation takes place without formation of significant amounts of by-products. In the case of a corresponding reaction of these ammonium salts in a flow tube with thermal jacket heating, only low conversions to the amide are achieved, although significant amounts of esters and ester amides are formed simultaneously. In addition, the extremely high wall temperatures required to achieve suitable reaction temperatures lead to decomposition reactions and the formation of colored species.

To complete the reaction, it has been found to be useful in many cases to expose the resulting crude product, after removal of water of reaction and optionally discharging product and/or by-product, again to microwave irradiation.

Typically, alkanolamides prepared via the inventive route are obtained in a purity sufficient for further use. For specific requirements, they can, however, be purified further by customary purification processes such as distillation, recrystallization, filtration, or via chromatographic processes.

The basic amides prepared in accordance with the invention are suitable, for example, as emulsifiers, in the mineral oil industry as corrosion or gas hydrate inhibitors, and as lubricity improvers in lubricant and fuel oils, and in metal processing as cooling lubricants. Any terminal hydroxyl groups present may, if required, subsequently be derivatized further, for example by esterification, etherification and other known reactions.

The process according to the invention allows very rapid and inexpensive preparation of fatty acid alkanolamides in high yields and with high purity. More particularly, they have only a low content of alkanolamine esters and of ester amides. Their aqueous solutions are therefore clear and have, in contrast to the corresponding fatty acid alkanolamides prepared by thermal condensation, no cloudiness caused by ester amides. The intrinsic color of the amides prepared in accordance with the invention corresponds to Hazen color numbers (to DIN/ISO 6271) of less than 200 and in some cases less than 150, for example less than 100, whereas Hazen color numbers less than 250 are not obtainable without additional process steps by conventional methods. Furthermore, no significant amounts of by-products are obtained, for example decarboxylated carboxylic acids. Such rapid and selective reactions cannot be achieved by conventional methods and were also not to be expected solely through heating to high temperatures. Since the alkanolamides prepared by the process according to the invention additionally, as a result of the process, do not contain any residues of coupling reagents or conversion products thereof, they can also be used without any problem in toxicologically sensitive areas, for example cosmetic and pharmaceutical formulations.

EXAMPLES

The reactions under microwave irradiation were effected in a CEM "Discover" single-mode microwave reactor at a frequency of 2.45 GHz. The reaction vessels were cooled by means of compressed air. The temperature was measured by means of an IR sensor at the base of the cuvette. Owing to the pressure conditions in the reaction vessel, the temperatures had to be measured by means of an IR sensor at the base of the cuvette. Comparative tests with a glass fiber optic immersed into the reaction mixture found that the temperature in the reaction medium, within the temperature range relevant here, is about 50 to 80° C. above the temperature measured with the IR sensor at the base of the cuvette.

The batchwise reactions were effected in closed, pressure-resistant glass cuvettes with a volume of 8 ml with magnet stirring. Continuous reactions were effected in pressure-resistant, cylindrical glass cuvettes configured as a jacketed tube (approx. 10×1.5 cm; reaction volume 15 ml) with an internal inlet tube (base inlet) ending above the base of the cuvette, and product removal at the upper end of the cuvette. The pressure which builds up during the reaction was limited to a maximum of 20 bar by means of a pressure-retaining valve and released into a reservoir. The ammonium salt was pumped into the cuvette through the inlet tube, and the residence time in the irradiation zone was adjusted by modifying the pump output.

The products were analyzed by means of $^1$H NMR spectroscopy at 500 MHz in $CDCl_3$. Water determinations were effected by means of Karl-Fischer titration. Hazen color numbers were determined to DIN/ISO 6271.

Example 1

Preparation of coconut fatty acid monoethanolamide 1.5 g of ethanolamine were admixed slowly with 5.0 g of molten coconut fatty acid with cooling and stirring. After the exothermicity had abated, the ammonium salt thus obtained was exposed to microwave irradiation of 200 W in a closed cuvette with maximum cooling performance for 10 minutes. A temperature of 195° C. measured by means of an IR sensor was attained, and the pressure rose to 10 bar.

The resulting crude product contained, as main components, 85% coconut fatty acid monoethanolamide, 5.4% water and unconverted reactants. After the reaction mixture had been dried over $MgSO_4$, irradiated with 200 W microwaves for another 5 minutes and dried over $MgSO_4$, a yield of coconut fatty acid monoethanolamide of more than 98% was obtained. The coconut fatty acid monoethanolamide thus obtained contained less than 1 mol % of amino ester and ester amide. The Hazen color number was 80 (undiluted molten product).

Example 2

Preparation of Lauric Acid Diethanolamide

At 50° C., 2.5 g of diethanolamine were admixed slowly with 4.6 g of molten lauric acid with stirring. After the exothermicity had abated, the ammonium salt thus obtained was exposed to microwave irradiation of 200 W in a closed cuvette with maximum cooling performance for 10 minutes. A temperature of 190° C. measured by means of an IR sensor was attained, and the pressure rose to 10 bar.

The crude product contained 78% lauric acid diethanolamide as the main component, 4.5% water and unconverted reactants. After the reaction mixture had been dried over $MgSO_4$ and irradiated with 200 W microwaves for another five minutes, and water of reaction and excess diethanolamine had been removed by distillation under reduced pressure, a yield of lauric acid diethanolamide of more than 97% was obtained. The resulting coconut fatty acid diethanolamide contained about 1 mol% of amino ester and ester amide. The Hazen color number was 120 (undiluted molten product).

Example 3

Preparation of N-lauroyl-2-(2-aminoethoxy)ethanol 2.5 g of 2-(2-aminoethoxy)ethanol were admixed slowly with an equimolar amount of lauric acid with cooling and stirring. After the exothermicity had abated, the ammonium salt thus obtained was exposed to microwave irradiation of 150 W in a closed cuvette with maximum cooling performance for 5 minutes. A temperature of 200° C. measured by means of an IR sensor was attained, and the pressure rose to 12 bar.

The crude product contained 80% N-lauroyl-2-(2-aminoethoxy)ethanol as the main component, 4.7% water and unconverted reactants. After the reaction mixture had been dried over $MgSO_4$, irradiated with 150 W microwaves for another two minutes and dried, N-lauroyl-2-(2-aminoethoxy)ethanol was obtained with more than 97% yield. The resulting N-lauroyl-2-(2-aminoethoxy)ethanol contained less than 1 mol% of amino ester and ester amide The Hazen color number was 90 (undiluted product).

Example 4

Continuous Preparation of Coconut Fatty Acid Diethanolamide 105 g of diethanolamine were admixed slowly at 40° C. with 205 g of coconut fatty acid with cooling and stirring. After the exothermicity had abated, the ammonium salt thus obtained was pumped continuously via the bottom inlet through the pressure-resistant glass cuvette mounted in the microwave cavity. The delivery output of the pump was adjusted such that the residence time in the cuvette and hence in the radiation zone was about 2 minutes. Maximum cooling performance was employed with a microwave power of 200 W, and a temperature of 180° C. measured by means of an IR sensor was attained. After leaving the glass cuvette, the reaction mixture was cooled to 40° C. by means of a short Liebig condenser.

After the water of reaction had been removed, the crude product was pumped through the glass cuvette once again as above and exposed again to microwave radiation. After the water of reaction had been removed, coconut fatty acid diethanolamide was obtained with more than 97% yield. No ester components were detectable. The resulting coconut fatty acid diethanolamide contained less than 1 mol % of amino ester and ester amide. The Hazen color number of this amide was 90 (undiluted product).

Example 5

Continuous Preparation of Coconut Fatty Acid Propanolamide 75 g of propanolamine (1 mol) were admixed slowly at 40° C. with 214 g (1 mol) of coconut fatty acid with cooling and stirring. After the exothermicity had abated, the ammonium salt thus obtained was pumped continuously via the bottom inlet through the pressure-resistant glass cuvette mounted in the microwave cavity. The delivery output of the pump was adjusted such that the residence time in the cuvette and hence in the irradiation zone was about 1.5 minutes. Maximum cooling performance was employed with a microwave power of 300 W, and a temperature of 195° C. measured by means of an IR sensor was attained. After leaving the glass cuvette, the reaction mixture was cooled to about 100° C. by means of a short Liebig condenser and then the water of reaction was removed under reduced pressure.

After the unconverted isopropanol which had likewise been removed had been replaced, the crude product was pumped through the glass cuvette once again as above and exposed again to microwave radiation. After the water of reaction had been removed again, coconut fatty acid propanolamide was obtained with more than 95% yield. According to the $^1$H NMR spectrum, the product still contained about 3% unreacted coconut fatty acid; the concentrations of any further by-products (e.g. esters, ester amides) were below the detection limit. The Hazen color number of this amide was 70 (undiluted, molten product).

Example 6

Continuous Preparation of Tall Oil Fatty Acid Diglycolamide 119 g of diglycolamine (1 mol) were admixed slowly at 50° C. with 280 g (1 mol) of tall oil fatty acid with cooling and stirring. After the exothermicity had abated, the ammonium salt thus obtained was pumped continuously via the bottom inlet through the pressure-resistant glass cuvette mounted in the microwave cavity. The delivery output of the pump was adjusted such that the residence time in the cuvette and hence in the irradiation zone was about 2.5 minutes. Maximum cooling performance was employed with a microwave power of 200 W, and a temperature of 190° C. measured by means of an IR sensor was attained. After leaving the glass cuvette, the reaction mixture was cooled to about 100° C. by means of a short Liebig condenser and then the water of reaction was removed under reduced pressure. The crude product was subsequently pumped twice more through the glass cuvette as described above while again being exposed to microwave radiation, and then freed from the water of reaction each time.

After the reaction mixture had thus been irradiated three times with microwaves, a tall oil fatty acid diglycolamide was obtained with a purity of 96% ($^1$H NMR). According to the $^1$H NMR spectrum, the product still contained about 2% unreacted tall oil fatty acid; the concentrations of any further by-products (e.g. esters, ester amides) were below the detection limit. The Hazen color number of this amide was 80.

Example 7

Continuous Thermal Reaction of Lauric Acid With Ethanolamine (Comparative Example)

61 g of ethanolamine (1 mol) were admixed slowly with 214 g of lauric acid (1 mol) with cooling and stirring. After the exothermicity had abated, the ammonium salt thus obtained was pumped continuously via the bottom inlet through a pressure-resistant glass cuvette present in an oil bath at 250° C. The delivery output of the pump was adjusted such that the residence time of the reactants in the cuvette and hence in the reaction zone was about 90 seconds. A temperature measurement was undertaken at the overflow of the cuvette. The maximum temperatures observed here were 190° C. After leaving the glass cuvette, the reaction mixture was cooled to room temperature by means of a short Liebig condenser.

With the aid of this continuous mode of operation using a conventional heating medium, only conversions of 10% to the desired product were achievable. In addition, 3% of the corresponding ester was detected in the $^1$H NMR. Ester amides as a by-product were not unambiguously identifiable owing to the low conversion. The Hazen color number of this reaction product was 280.

The invention claimed is:
1. A process for preparing a fatty acid alkanolamide by reacting at least one amine, which contains at least one secondary amino group and at least one hydroxyl group, wherein the amine corresponds to the formula

$HNR^1R^2$, and wherein
$R^1$ is a group of the formula $—(B—O)_m—H$
B is an alkylene radical having 2 to 10 carbon atoms,
m is from 1 to 500 and
$R^2$ is $R^1$ or a hydrocarbon radical having 1 to 50 carbon atoms,
with at least one fatty acid to give an ammonium salt, and subsequently further converting the ammonium salt under microwave irradiation to the fatty acid alkanolamide.

2. The process as claimed in claim 1, wherein the fatty acid comprises an aliphatic, hydrocarbon radical having 1 to 50 carbon atoms.

3. The process as claimed in claim 2, wherein the hydrocarbon radical comprises at least one substituent selected from the group consisting of: halogen atoms, halogenated alkyl radicals, cyano, hydroxyalkyl, hydroxyl, methoxy, nitrite, nitro and sulfonic acid groups.

4. The process as claimed in claim 2, wherein the hydrocarbon radical is saturated.

5. The process as claimed in claim 1, wherein the hydrocarbon radical comprises at least one double bond.

6. The process as claimed in claim 1, wherein the fatty acid is selected from the group consisting of: octanoic acid, decanoic acid, dodecanoic acid, tridecanoic acid, tetradecanoic acid, 12-methyltridecanoic acid, pentadecanoic acid, 13-methyltetraclecanoic acid, 12-methyltetradecancic acid, hexadecanoic acid, 14-methylpentadecanoic acid, heptadecanoic acid, 15-methylhexadecanoic acid, 14-methylhexadecanoic acid, octadecanoic acid, isooctadecanoic acid, eicosanoic acid, docosanoic acid, tetracosanoic acid, myristoleic acid, paimitoleic acid, hexadecadienoic acid, delta-9-cis-heptadecenoic acid, oleic acid, petroselic, acid, vaccenic acid, linaleic acid, linolenic acid, gadoleic acid, gondoleic acid, eicosadienoic acid, arachidonic acid, cetoleic acid, erucic acid, docosadienoic acid, tetracosenoic acid, ricinoleic acid, tall oil fatty acid, resin acids and naphthenic acids.

7. The process as claimed in claim 1, wherein the amine is selected from the croup consisting of: N-methylaminoethanol, N-ethylaminoethanol, N-butylethanolamine, N-methylisopropanoiamine, diethanolamine, dipropanolamine, diisopropanolamine and di(diethylene glycol)amine.

8. The process as claimed in claim 1, wherein the microwave irradiation is performed in the presence of a dehydrating catalyst.

9. The process as claimed in claim 1, wherein the process is performed in the presence of a solvent.

10. The process as claimed in claim 9, wherein the solvent has a dielectric loss value of less than 10.

11. The process as claimed in claim 1, wherein the process is performed at temperatures below 300° C.

12. The process as claimed in claim 1, wherein the reaction is performed at at least one pressure between 0.1 and 200 bar.

13. The process as claimed in claim 1, wherein the reaction is effected continuously by irradiating with microwaves in a reaction tube through which the ammonium salt flows.

14. The process as claimed in claim 13, wherein the reaction tube consists of a nonmetallic microwave-transparent material.

15. The process as claimed in claim 13, wherein the residence time of the reaction mixture in the reaction tube is less than 30 minutes.

16. The process as claimed in claimed 13, wherein the reaction tube has a ratio of length to diameter of at least 5, $R^1$ is a group of the formula

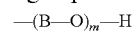

wherein
B is an alkylene radical having 2 to 10 carbon atoms and m is from 1 to 500.

17. The process as claimed in claim 1. wherein B is a linear alkylene radical having 2 to 5 carbon atoms.

* * * * *